United States Patent
Eder et al.

(10) Patent No.: US 9,289,181 B2
(45) Date of Patent: Mar. 22, 2016

(54) PATIENT SUPPORT APPARATUS, A MEDICAL IMAGING APPARATUS WITH THE PATIENT SUPPORT APPARATUS AND A METHOD FOR MARKING A MAXIMUM OCCUPANCY AREA

(71) Applicants: Hanns Eder, Bubenreuth (DE); Patrick Gross, Buckenhof (DE); Martin Ringholz, Erlangen (DE)

(72) Inventors: Hanns Eder, Bubenreuth (DE); Patrick Gross, Buckenhof (DE); Martin Ringholz, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 0 days.

(21) Appl. No.: 13/892,487

(22) Filed: May 13, 2013

(65) Prior Publication Data
US 2013/0298329 A1 Nov. 14, 2013

(30) Foreign Application Priority Data
May 14, 2012 (DE) .................. 10 2012 208 037

(51) Int. Cl.
*A61B 6/04* (2006.01)
*A61B 6/10* (2006.01)
*A61G 13/00* (2006.01)
(Continued)

(52) U.S. Cl.
CPC .............. *A61B 6/0492* (2013.01); *A61B 6/0407* (2013.01); *A61B 6/0421* (2013.01); *A61B 6/102* (2013.01); *A61B 6/501* (2013.01); *A61G 13/0018* (2013.01); *A61G 13/121* (2013.01); *A61B 5/704* (2013.01); *A61B 6/032* (2013.01); *A61B 6/037* (2013.01); *A61B 6/4441* (2013.01); *A61G 2203/72* (2013.01)

(58) Field of Classification Search
CPC ........ A61B 6/04; A61B 6/102; A61B 6/0407; A61B 6/0492; A61B 5/704; A61B 5/0555; A61B 6/501; A61B 6/0421; A61B 6/037; A61B 6/4441; A61B 6/032; A61G 7/072; A61G 7/121; A61G 2203/22; A61G 2203/72; A61G 2210/50; A61G 13/121; A61G 13/0018
USPC ........ 5/600, 601, 606, 86.1, 81.1 R, 621–624; 378/209; 600/415
See application file for complete search history.

(56) References Cited

U.S. PATENT DOCUMENTS 5,160,337 A 11/1992 Cosman
5,207,223 A * 5/1993 Adler ............................ 600/427
(Continued)

FOREIGN PATENT DOCUMENTS

DE 19743500 A1 4/1999
DE 102005057371 A1 6/2007

OTHER PUBLICATIONS http://www.noras.de/download/Datenblatt_OR_Kopfhalter.pdf.
(Continued)

*Primary Examiner* — Nicholas Polito
*Assistant Examiner* — David R Hare

(57) ABSTRACT

Disclosed is a patient support apparatus having a patient support couch, a moveable support plate for supporting a patient, a surgical head fastening unit for fastening a head of the patient in an examination position and/or in an operation position. The patient support apparatus includes a marker unit for marking a maximum occupancy area for the surgical head fastening unit.

9 Claims, 2 Drawing Sheets

(51) Int. Cl.
    *A61G 13/12*     (2006.01)
    *A61B 5/00*     (2006.01)
    *A61B 6/03*     (2006.01)
    *A61B 6/00*     (2006.01)

(56) References Cited

U.S. PATENT DOCUMENTS

| | | | | |
|---|---|---|---|---|
| 5,485,502 | A * | 1/1996 | Hinton et al. | 378/117 |
| 5,865,780 | A * | 2/1999 | Tuite | 602/32 |
| 5,878,112 | A * | 3/1999 | Koertge | 378/209 |
| 6,138,302 | A * | 10/2000 | Sashin et al. | 5/600 |
| 6,272,368 | B1 * | 8/2001 | Alexandrescu | 600/407 |
| 6,651,279 | B1 * | 11/2003 | Muthuvelan | 5/600 |
| 7,000,271 | B2 * | 2/2006 | Varadharajulu | 5/610 |
| 7,046,765 | B2 * | 5/2006 | Wong et al. | 378/117 |
| 8,442,617 | B2 * | 5/2013 | Scarth et al. | 600/415 |
| 8,745,789 | B2 * | 6/2014 | Saracen et al. | 5/601 |
| 8,873,709 | B2 * | 10/2014 | Kimura | 378/62 |
| 2006/0133573 | A1 | 6/2006 | Sayeh | |
| 2009/0003975 | A1 | 1/2009 | Kuduvalli | |
| 2009/0074151 | A1 | 3/2009 | Henderson | |
| 2009/0281452 | A1 * | 11/2009 | Pfister et al. | 600/567 |
| 2011/0006230 | A1 * | 1/2011 | Fadler | 250/522.1 |
| 2011/0170668 | A1 * | 7/2011 | Ozawa et al. | 378/98.5 |
| 2012/0014513 | A1 * | 1/2012 | Watanabe et al. | 378/209 |
| 2013/0281818 | A1 * | 10/2013 | Vija et al. | 600/407 |
| 2013/0315381 | A1 * | 11/2013 | Dong | 378/209 |
| 2013/0340165 | A1 * | 12/2013 | Dong et al. | 5/601 |
| 2014/0022353 | A1 * | 1/2014 | Hamersma et al. | 348/46 |

OTHER PUBLICATIONS http://www.gehealthcare.com/usen/mr/docs/Surg_Suite.pdf.
www.brainlab.com/art/2844/intra-operative-mri/.
http:www.imris.com/product/neurosurgery.

* cited by examiner

PATENT SUPPORT APPARATUS, A MEDICAL IMAGING APPARATUS WITH THE PATIENT SUPPORT APPARATUS AND A METHOD FOR MARKING A MAXIMUM OCCUPANCY AREA

CROSS REFERENCE TO RELATED APPLICATIONS

This application claims priority of German application No. 102012208037.6 filed May 14, 2012. All of the applications are incorporated by reference herein in their entirety.

FIELD OF INVENTION

The present invention relates to a patient support apparatus having a patient support couch, a moveable support plate for supporting a patient and a surgical head fastening unit for fastening a head of the patient in an examination position and/or in an operation position.

BACKGROUND OF INVENTION

For neurosurgical interventions, it is usual for the patient to be positioned on a moveable support plate of a patient support apparatus. In this way the head of the patient is in particular fixed within a surgical head fastening unit in order to obtain a securely fastened operation position and/or examination position of the head. In this position fixed within the surgical head fastening unit, the patient is also introduced into medical imaging apparatuses for a medical imaging examination by means of the moveable support plate. The medical imaging apparatus can herewith be formed for instance of in particular a magnetic resonance apparatus and/or a computed tomography apparatus and/or a PET apparatus and/or a C-arm apparatus etc. It is however necessary in this process to match a position of the surgical head fastening unit in respect of the moveable support plate and a dimension of an opening of the medical imaging apparatus in order to receive the patient.

Such a matching of the position of the surgical head fastening unit previously took place in accordance with a rough estimation of a clinical operating personnel. It may nevertheless herewith result in the surgical head fastening unit colliding with a housing wall of the medical imaging apparatus and/or the surgical head fastening unit must be aligned and positioned again together with the patient prior to a collision. This is nevertheless very complex in terms of work flow and unpleasant for clinical operating personnel. In addition, this brings about a high risk of infection and/or a high risk of injury to the patient.

SUMMARY OF INVENTION

The object underlying the present invention is in particular to provide a patient support apparatus with a surgical head fastening unit, in which a secure and rapid positioning and/or fixing of a head of the patient can be achieved by means of the surgical head fastening unit within a permissible occupancy area for a medical imaging examination. The object is achieved by the features of the independent claims Advantageous embodiments are described in the dependent claims.

The invention is based on a patient support apparatus having a patient support couch, a moveable support plate for supporting a patient and a surgical head fastening unit for fastening a head of the patient in an examination position and/or an operation position.

It is proposed that the patient support apparatus comprises a marker unit for marking a maximum occupancy area for the surgical head fastening unit. The maximum occupancy area for the surgical head fastening unit may be shown as visible to the clinical operating personnel and a simple and rapid positioning and/or fixing of the head of the patient together with the surgical head fastening unit to the moveable support plate can herewith be achieved in an examination position and/or an operation position. Furthermore, the patient, together with the surgical head fastening unit, can be securely introduced into the medical imaging apparatus for a subsequent medical imaging examination. Furthermore, a time-saving and/or cost-saving preparation of the patient, in particular positioning of the patient, can also advantageously be achieved and in the process a work flow for the clinical operating personnel can be advantageously optimized The maximum occupancy area essentially orthogonal to a reclining surface of the moveable support plate is particularly advantageous here and in addition essentially orthogonal to a longitudinal extension of the moveable support plate. A size and shape of the maximum occupancy area preferably essentially correspond to a sixe and shape of a cross-sectional surface of an opening area of a receiving area for receiving the patient of a medical imaging apparatus. In this context, the term examination position and/or operation position should be understood in particular to mean a position of the head of the patient within the surgical head fastening unit, wherein the head of the patient is to this end firstly fixed in the operation position for an operation and/or a surgical intervention and after and/or during the operation and/or the surgical intervention, control of the operation and/or the surgical intervention takes place by means of a medical imaging examination, wherein the patient is to this end arranged in the examination position, which is identical to the operation position, in the surgical head fastening unit within an examination region of a medical imaging apparatus.

In this context a maximum occupancy area for the surgical head fastening unit should be understood in particular to mean an occupancy area, the extent of which essentially corresponds to a maximum extent of an opening of a receiving area for receiving the patient for a medical imaging examination of the medical imaging apparatus less a safety area and/or tolerance range. In this way when the maximum occupancy area is retained during the positioning of the surgical head fastening unit, the risk of the surgical head fastening unit colliding with a detector unit of the medical imaging apparatus and/or a housing surrounding the receiving area of the medical imaging apparatus are advantageously minimized. The head of the patient is preferably fixedly fixed within the surgical head fastening unit, so that a movement of the head and/or unwanted change in position of the head can be ruled out. The surgical head fastening unit can also comprise a sterile cover, which after positioning and/or fixing the head of the patient within the surgical head fastening unit is arranged above the head area of the patient. A work flow for positioning and/or fixing the head of the patient within the surgical head fastening unit can advantageously be optimized by means of the marker unit, so that a repeated, in particular time-consuming removal of the cover and repositioning of the surgical head fastening unit can be prevented. If an area of the surgical head fastening unit lies outside of the marker and/or the maximum occupancy area, this is an indication to clinical operating personnel of a possible risk of collision when introducing the patient into the medical imaging apparatus. Marking of the maximum occupancy area is to be understood in particular as marking at least a subarea of the maximum occupancy area.

It is furthermore proposed for the marker unit to comprise at least one marker element, which marks at least a border area of the maximum occupancy area in a critical collision area of the surgical head fastening unit. The clinical operating personnel can herewith be particularly rapidly referred to an unwanted faulty positioning at critical and/or high risk collision areas of the surgical head fastening unit. Furthermore, marking the border area can achieve a particularly cost-effective marking of the maximum occupancy area, since occupancy within the border area and/or transgressing the border area already points to a faulty positioning of the surgical head fastening unit. The critical collision area may include corner areas and/or border areas and/or a maximum expansion area of the surgical head fastening unit. In addition, a position correction of this type can be implemented prior to the medical imaging examination so that an optimized work flow can take place, which enables prompt recognition of a possible risk of collision and in such a way the clinical operating personnel can also promptly respond to the possible risk of collision. For instance, it is herewith possible to dispense with a repeated positioning and sterile coverage of the patient which follows respectively. In addition, costs can herewith be advantageously saved, since sterile coverage can take place by means of one-way sterile covers, which cannot be used after initial attachment and only one single sterile cover must to be used for one examination by means of the inventive apparatus.

In an advantageous development of the invention, it is proposed that the marker unit comprises at least one marker element, which is arranged in a front area of the patient support couch and/or the moveable support plate. An advantageous marking can herewith be achieved in a possible collision area and/or danger area since this possible collision area and/or danger area is preferably also arranged in this front area of the moveable support plate. A front area of the patient support couch and/or the moveable support plate of the patient support apparatus is in this context understood to mean in particular an area for supporting a head of the patient. Particularly advantageous however is the marker unit in the front area of the moveable support plate, so that upon exchange of the moveable support plate between two different patient support apparatus and/or an operation table independent of a positioning and/or arrangement of the moveable support plate, a marking of the permissible occupancy area can in particular take place in order to set and/or adjust the surgical head fastening unit.

It is particularly advantageous if the at least one marker element is arranged in an overlay area of the border area of the maximum occupancy area with the front area of the patient support table and/or the moveable support plate, whereby a structurally simple marking of a possible collision area and/or danger area can be achieved. It is particularly advantageous here for the at least one marker element to be arranged on the patient support couch and/or on the moveable support plate such that the marker element, together with the border area of the maximum occupancy area of the surgical head fastening unit and a border area of the opening of the receiving area of the medical imaging apparatus are arranged on a straight line irrespective of a distance of the patient support apparatus from the medical imaging apparatus, so that it is possible to dispense with a time-consuming adjustment of the marker unit along at least one direction.

In a further embodiment of the invention, it is proposed that the marker unit is formed of an illumination unit, as a result of which a particularly simple and cost-effective marking of the maximum occupancy area can be achieved. In addition, an advantageous, optical representation of the marking can be achieved for the operator.

The illumination unit herewith particularly advantageously comprises a laser unit, as a result of which an advantageous marking of the maximum occupancy area can be achieved. In particular, the laser unit to this end includes a fan laser unit. The fan laser unit is preferably designed for this purpose to divide a laser beam into a fan-shaped arrangement of individual partial laser beams, wherein the fan-shaped arrangement of the individual partial laser beams preferably at least partially marks and/or illuminates the border area of the maximum occupancy area. Alternatively, the fan laser unit can also comprise a single laser beam, which illuminates a fan-type area with a high illumination frequency so that an essentially simultaneous illumination of the entire fan-type area is achieved to the eyes of the observer. The fan laser unit is preferably designed to illuminate and/or mark the maximum occupancy area and/or the border area of the maximum occupancy area along at least two different directions. To this end the marker unit particularly advantageously comprises at least two or more laser units, in particular fan laser units, so that the complete border area of the maximum occupancy area of the head fastening unit is illuminated and/or marked as far as possible.

For supply with electrical energy, the marker unit can be connected to a central power supply of the patient support apparatus, in particular the patient support couch and/or the moveable support plate. The marker unit particularly advantageously however comprises at least one energy storage unit for storing electrical energy, so that the marker unit can also be operated independently of a power supply of the patient support apparatus.

In an advantageous development of the invention, it is proposed for the marker unit to comprise an adjustment unit, so that a rapid setting and/or adjustment of the maximum occupancy area can be achieved. In addition, the marker unit, together with the patient support apparatus, can be used for different medical imaging devices.

Furthermore, the invention is also based on a medical imaging apparatus having a patient support apparatus.

It is proposed that the medical imaging apparatus comprises a receiving area for receiving a patient positioned on the patient support apparatus, wherein the receiving area comprises an opening, and the maximum occupancy area for the surgical head fastening unit is determined as a function of an opening area of the opening. The maximum occupancy area of the surgical head fastening unit can be made visible to the clinical operating personnel and a simple and rapid positioning and/or fixing of the head of the patient together with the surgical head fastening unit on the moveable support plate can herewith be achieved in an examination position and/or an operation position. In addition, the patient, together with the surgical head fastening unit, can be safely introduced into the medical imaging apparatus for a subsequent medical imaging examination. Furthermore, a time-saving and/or cost-saving preparation of the patient, in particular positioning of the patient, can be advantageously achieved and in this way a work flow for the clinical operating personnel can be advantageously optimized. In addition, the clinical operating personnel can be referred particularly quickly to an unwanted faulty positioning at critical and/or high-risk collision areas of the surgical head fastening unit, so that the clinical operating personnel can immediately perform a change in position of the surgical head fastening unit.

Furthermore, the invention is based on a method for marking a maximum occupancy area for a surgical head fastening unit on a patient support apparatus, including the following method steps:

determining the maximum occupancy area, transmitting the maximum occupancy area to an area of the surgical head fastening unit and marking the maximum occupancy area in the region of the surgical head fastening unit.

The maximum occupancy area for the surgical head fastening unit can herewith be made visible to the clinical operating personnel and a simple and rapid positioning and/or fixing of the head of the patient, together with the surgical head fastening unit, to the moveable support plate in the examination position and/or the operation position can herewith be achieved. Furthermore, the patient, together with the surgical head fastening unit, can be safely introduced into the medical imaging apparatus for a subsequent medical imaging examination. Furthermore, a time-saving and/or cost-saving preparation of the patient, in particular positioning of the patient, can advantageously be achieved.

BRIEF DESCRIPTION OF THE DRAWINGS

Further advantages, features and details of the invention result from the exemplary embodiment described below and with the aid of the drawings, in which.

DETAILED DESCRIPTION OF INVENTION

Figure 1:
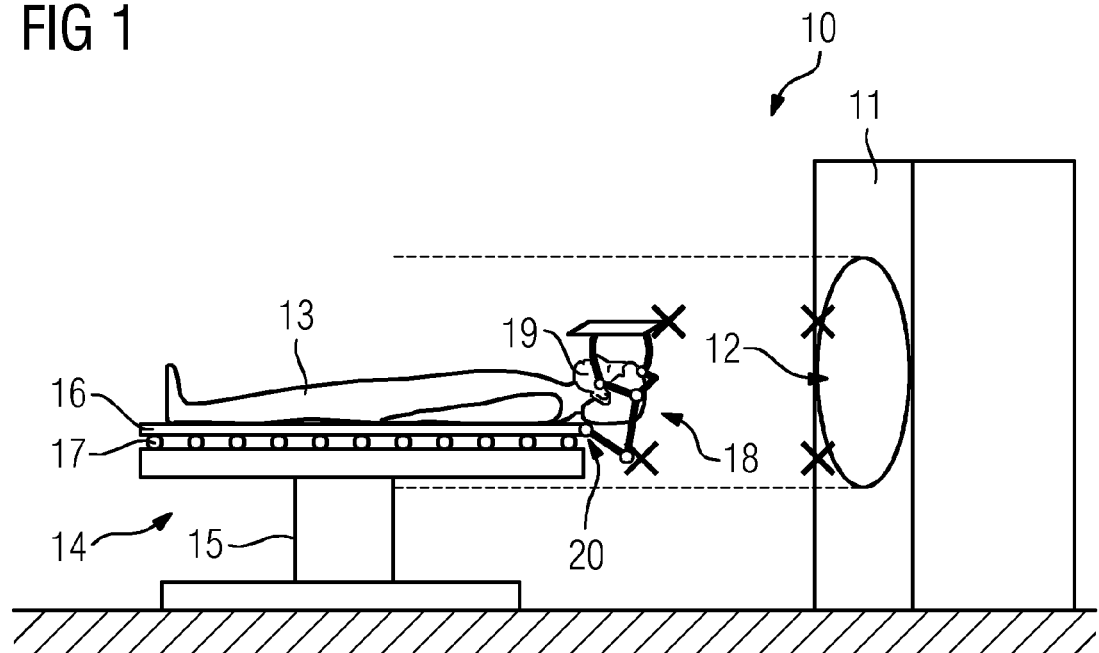
FIG. 1 shows a medical imaging apparatus in a schematic representation.

FIG. 1 shows a medical imaging apparatus 10. The medical imaging apparatus may be formed for instance of a magnetic resonance apparatus, a computed tomography apparatus, a positron emission tomography apparatus (PET apparatus), a C-arm apparatus etc.

The medical imaging apparatus 10 comprises a detector unit 11 and a receiving area 12 for receiving a patient 13 for a medical imaging examination, wherein the receiving area 12 is surrounded cylindrically by the detector unit 11. Furthermore, the medical imaging apparatus 10 includes a patient support apparatus 14 for supporting the patient for the medical imaging examination.

Figure 2:
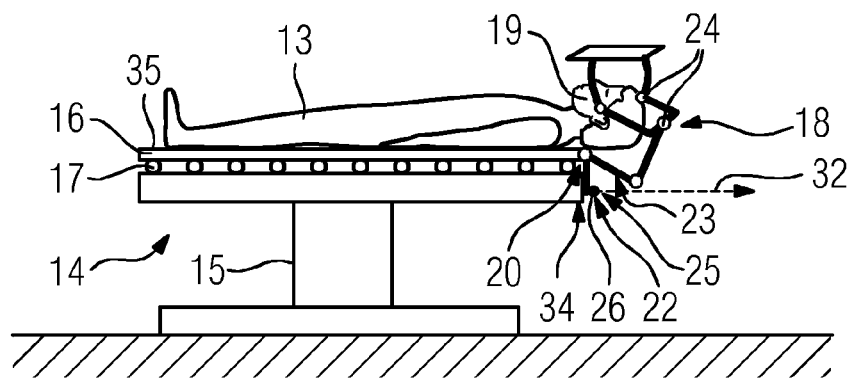
FIG. 2 shows an inventive patient support apparatus in a side view.
Figure 3:
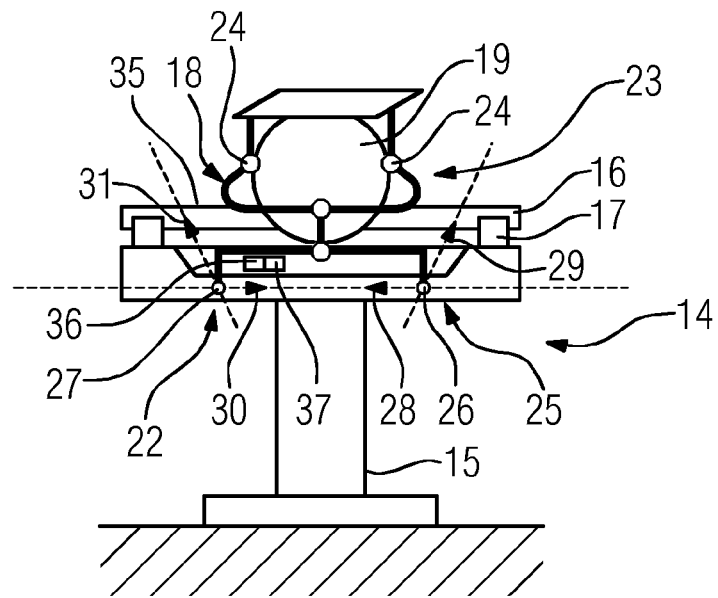
FIG. 3 shows the inventive patient support apparatus in a front view.

The patient support apparatus 13 is shown in more detail in FIGS. 2 and 3 and comprises a patient support couch 15 and a moveable support plate 16. The support plate 16 is herewith embodied to be moveable in respect of the patient support couch 15, wherein to this end the patient support apparatus 14 comprises a guiding unit and/or bearing unit 17. Aside from the moveable support plate 16, the patient support couch 15 can also be embodied to be moveable, such as is advantageous in particular in patient support apparatus 14, by means of which the patient can be transported from an operating couch to the medical imaging apparatus 10. It is furthermore also conceivable for the patient support apparatus 14 to include an operating couch and/or for the moveable support plate 16 to be exchanged between the patient support couch 15 and an operating couch.

Furthermore, the patient support apparatus 14 comprises a surgical head fastening unit 18 for fastening and/or fixing a head 19 of the patient 13 in an examination position and/or an operation position. The surgical head fastening unit 18 is arranged on a front area 20 of the moveable support plate 16 of the patient support apparatus 14. The patient support apparatus 14 further comprises a marker unit 22 for marking a maximum occupancy area 23 for the surgical head fastening unit 18.

For a surgical intervention on a head 19 of the patient 13 using a subsequent medical imaging examination, the patient 13 is positioned on the moveable support plate 16 for the surgical intervention, wherein the head 19 of the patient 13 is fixed in the surgical head fastening unit 18 in an examination position and/or an operation position. To this end, the surgical head fastening unit 19 comprises a number of setting means 24 for positioning and/or setting the surgical head fastening unit 18 in the examination position and/or operation position. For the subsequent medical imaging examination, the patient 13 is introduced in the fixed examination position and/or the fixed operation position into the receiving area 12 by means of the moveable support plate 16. In order during the introduction of the patient 13, together with the surgical head fastening unit 18, to prevent a possible collision between the patient 13 and/or the surgical head fastening unit 18 and a housing of the medical imaging apparatus 10 surrounding the receiving area 12 and/or the detector unit 11 of the medical imaging apparatus 10, a maximum occupancy area 23 for the surgical head fastening unit 18 is already marked during the positioning of the patient 13 on the moveable support plate 16, in particular during the fixing of the head 19 of the patient 13 by means of the surgical head fastening unit 8, by means of the marker unit 22.

The marker unit 22 to this end includes an optical marker unit, which, in the present exemplary embodiment, is formed of an illumination unit. The illumination unit includes a laser unit 25, which, in the present exemplary embodiment, is formed of a fan laser unit. Alternatively or in addition, the marker unit 22 can also include further marker means appearing meaningful to the person skilled in the art for marking the maximum occupancy area 24 for the surgical head fastening unit 18.

In the present exemplary embodiment the fan laser unit includes two marker elements 26, 27 embodied as fan laser elements, which each enable a fan-type arrangement of a laser beam and/or of partial laser beams To this end, the individual fan laser elements may comprise additional elements and/or means, which enable a fan-type division of the laser beam and/or a fan-type illumination by means of a single laser beam with a high illumination frequency. A marking and/or illumination of the maximum permissible occupancy area 23 is achieved in this way by means of the fan laser elements along different directions 28, 29, 30, 31, 32, wherein each of the fan laser elements emits a fan-type laser beam and/or partial laser beam along at least two different directions 28, 29, 30, 31, 32, preferably along three different directions 28, 29, 30, 31, 32, (FIGS. 2 and 3). Alternatively, the fan laser unit can to this end also comprise more than two fan laser elements and/or additionally the marker unit 22 can comprise further marker elements 26, 27. In addition, one embodiment of the fan laser unit is also conceivable with just one fan laser element.

During operation of the marker unit 22 and/or during positioning of the head 19 of the patient 13 and/or positioning of the surgical head fastening unit 18, illumination of a border area of the maximum occupancy area 23 for he surgical head fastening unit 18 takes place by means of the marker elements 26, 27, in particular of the fan laser elements. A subarea of the border area is herewith marked by means of the fan laser unit during the marking of the border area of the maximum occupancy area 23. This subarea of the border area includes the critical collision area of the surgical head fastening unit 18 with the detector unit 11 and/or the housing of the medical imaging apparatus 10 surrounding the receiving area 12.

If a subarea of the surgical head fastening unit 18 and/or a subarea of the head 19 of the patient 13 is disposed within the illuminated border area during the position and/or adjustment of the surgical head fastening unit 18, the clinical operating personnel are thus indicated that during introduction of the patient 13 together with the surgical head fastening unit 18 into the receiving area 12 of the medical imaging apparatus 10, this area may result in an unwanted collision with a housing of the medical imaging apparatus surrounding the receiving area 12 and/or the detector unit 11.

The marker unit 22, in particular the fan laser unit, is arranged in the front area 20 of the moveable support plate 16. Alternatively, the marker unit 22, in particular the fan laser unit, can also be arranged in a front area 34 of the patient support couch 15 and/or be arranged on lateral areas of the patient support couch 15 and/or the moveable support plate 16. In addition, the two fan laser elements are arranged on the front area 20 of the moveable support plate 16 such that the fan laser elements are already arranged in an overlay area of the border area of the maximum occupancy area 23, in particular on an overlay area of a lower border area and/or a border area facing away from a reclining surface 35 of the moveable support plate, the maximum occupancy area 23.

Furthermore, the marker unit 22 comprises an energy storage unit 36 for storing electrical energy, such as for instance conventional, replaceable batteries, so that the marker unit 22 can be operated independently of a power supply of the patient support apparatus 14. Alternatively to this, the marker unit 22 can also be connected to a central power supply circuit of the patient support apparatus 14. The marker unit 22 also comprises an adjustment unit 37 for adjusting the two marker elements 26, 27. The maximum occupancy area 23 in a region of the surgical head fastening unit 18 is set by means of the adjustment unit 37. The maximum occupancy area 23 is to this end essentially orthogonal to the reclining surface 35 of the moveable support plate 16 and also essentially orthogonal to a longitudinal extension of the reclining surface 35. The adjustment unit 37 can be formed of an electronic adjustment unit 37, which can implement an essentially automatic adjustment and/or setting of the maximum occupancy area 23. Alternatively, the adjustment unit 37 can to this end also comprise adjustment elements, which enable a manual setting and/or adjustment of the maximum occupancy area 23 for the clinical operating personnel.

The maximum occupancy area 23 is determined by an opening area of the receiving area 12 for receiving the patient 13, wherein the occupancy area 23, together with a safety area, essentially comprises an expansion and/or size of the opening area of the receiving area 12. The safety area is herewith arranged about the maximum occupancy area 23.

Figure 4:
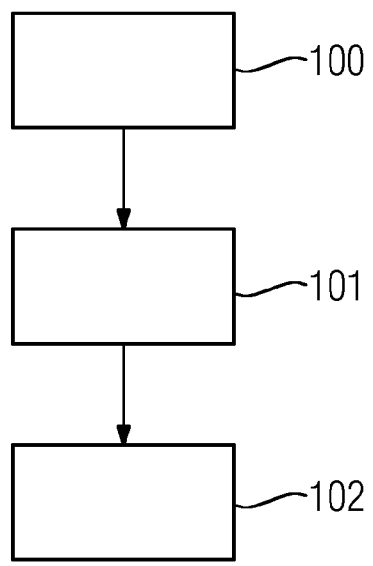
FIG. 4. shows an inventive method for marking a maximum occupancy area.

FIG. 4 shows a method for marking the maximum reclining surface 23 for the surgical head fastening unit 18. To mark the maximum occupancy area 23, the maximum occupancy area 23 is initially determined in a first method step 100. The opening area of the receiving area 12 is herewith detected and deducted from the safety area. In a further method step 101, the determined maximum occupancy area 23 is then transmitted to an area of the patient support apparatus 14, in which the surgical head fastening unit 18 is arranged. This area may include a maximum expansion of the surgical head fastening unit 18 for instance. The determined maximum occupancy area 23 for the surgical head fastening unit 18 is herewith transmitted unsealed to the area of the surgical head fastening unit 18.

With a subsequent positioning of the patient 13 on the moveable support plate 16 and a positioning of the head 19 of the patient 13 within the surgical head fastening unit 18, the border area of the maximum occupancy surface 23 is illuminated in a third method step 102 by means of the two marker elements 26, 27, in particular of the fan laser elements, so that this maximum occupancy area 23 for the surgical head fastening unit 18 is indicated to the clinical operating personnel performing the positioning. During the setting and/or positioning of the surgical head fastening unit 18, the clinical operating personnel is thus shown whether the surgical head fastening unit 18 retains the maximum occupancy area 23. As soon as the maximum occupancy area 23 is exceeded by the surgical head fastening unit 18, the surgical head fastening unit 18 is marked and/or illuminated in this region by the marker unit 22 and/or the fan laser unit, so that the clinical operating personnel can immediately perform a position correction.

While specific embodiments have been described in detail, those with ordinary skill in the art will appreciate that various modifications and alternative to those details could be developed in light of the overall teachings of the disclosure. For example, elements described in association with different embodiments may be combined. Accordingly, the particular arrangements disclosed are meant to be illustrative only and should not be construed as limiting the scope of the claims or disclosure, which are to be given the full breadth of the appended claims, and any and all equivalents thereof. It should be noted that the term "comprising" does not exclude other elements or steps and the use of articles "a" or "an" does not exclude a plurality.

The invention claimed is:

1. A patient support apparatus, comprising:
   a patient support couch;
   a moveable support plate for supporting a patient;
   a surgical head fastening unit for fastening a head of the patient in an examination position and/or in an operation position; and
   a marker unit for marking a maximum occupancy area for the surgical head fastening unit,
   wherein the marker unit comprises an adjustment unit for adjusting the maximum occupancy area,
   wherein the marker unit is formed by an illumination unit,
   wherein the illumination unit is arranged in an overlay area of a border area of the maximum occupancy area of the moveable support plate, and
   wherein the adjustment unit is adapted for adjusting the illumination unit.

2. The patient support apparatus as claimed in claim 1, wherein the maximum occupancy area is aligned orthogonally to a reclining surface of the moveable support plate.

3. The patient support apparatus as claimed in claim 1, wherein the marker unit marks the border area of the maximum occupancy area in a critical collision area of the surgical head fastening unit.

4. The patient support apparatus as claimed in claim 1, wherein the illumination unit includes a laser unit.

5. The patient support apparatus as claimed in claim 4, wherein the laser unit includes a fan laser unit.

6. The patient support apparatus as claimed in claim 1, wherein the marker unit comprises an energy storage unit for storing electrical energy.

7. A medical imaging apparatus comprising:
   a receiving area for receiving a patient;

a detector unit for a medical imaging examination of the patient; and
a patient support apparatus comprising:
   a patient support couch;
   a moveable support plate for supporting a patient;
   a surgical head fastening unit for fastening a head of the patient in an examination position and/or in an operation position; and
   a marker unit for marking a maximum occupancy area for the surgical head fastening unit,
      wherein the marker unit comprises an adjustment unit for adjusting the maximum occupancy area,
wherein the marker unit comprises an illumination unit,
wherein the illumination unit is arranged in an overlay area of a border area of the maximum occupancy area of the moveable support plate, and
wherein the adjustment unit is adapted for adjusting the illumination unit.

8. The medical imaging apparatus as claimed in claim 7, wherein the receiving area comprises an opening and the maximum occupancy area for the surgical head fastening unit is determined as a function of an opening area of the opening.

9. A method for marking a maximum occupancy area for a surgical head fastening unit on a patient support apparatus, the method comprising:
   determining the maximum occupancy area based on a receiving area for receiving a patient;
   transmitting the maximum occupancy area onto an area of the patient support apparatus in which the surgical head fastening unit is arranged;
   marking the maximum occupancy area for the surgical head fastening unit by a marker unit, the marker unit comprising an adjustment unit; and
   adjusting the maximum occupancy area by the adjustment unit;
   wherein the marker unit comprises an illumination unit,
   wherein the illumination unit is arranged in an overlay area of a border area of the maximum occupancy area of the moveable support plate, and
   wherein the adjustment unit is adapted for adjusting the illumination unit.

\* \* \* \* \*